United States Patent [19]

Sugiyama et al.

[11] Patent Number: 4,564,471

[45] Date of Patent: Jan. 14, 1986

[54] METHOD FOR REDUCTIVE ELIMINATION OF PROTECTING GROUPS

[75] Inventors: Katsumi Sugiyama; Hideo Takeda, both of Kawasaki; Hiroko Sato, Yokohama; Yuji Nonaka, Shinnanyo; Kiyotaka Oyama, Shinnanyo; Masashige Kubo, Shinnanyo, all of Japan

[73] Assignees: Ajinomoto Co., Inc.; Toyo Soda Mfg. Co., Ltd.; Sagami Chem. Rsch. Cntr., all of Japan

[21] Appl. No.: 188,107

[22] Filed: Sep. 17, 1980

[30] Foreign Application Priority Data

Sep. 27, 1979 [JP] Japan ............................ 54-123178

[51] Int. Cl.$^4$ ............................................. C07C 103/52
[52] U.S. Cl. ............................................... 260/112.5 K
[58] Field of Search ................................... 260/112.5 R

[56] References Cited

U.S. PATENT DOCUMENTS

| | | | |
|---|---|---|---|
| 3,798,204 | 3/1974 | Nakajima et al. | 260/112.5 R |
| 3,853,835 | 12/1974 | Mazur et al. | 260/112.5 R |
| 3,972,860 | 8/1976 | Moriarty et al. | 260/112.5 R |
| 4,017,472 | 4/1977 | Farkas et al. | 260/112.5 R |

OTHER PUBLICATIONS

Schroder et al., The Peptides, vol. I, pp. 26, 27, 1965.

H. T. Clarke et al., "A Handbook of Organic Analysis", (1975), p. 68.

Clarke et al., A Handbook of Organic Analysis, Fifth Edition, Edward Arnold (1968), pp. 65–67.

Primary Examiner—Delbert R. Phillips
Attorney, Agent, or Firm—Brisebois & Kruger

[57] ABSTRACT

The invention provides a novel and efficient method for the elimination of protecting groups, e.g. benzyloxycarbonyl group, from a protected amino acid, peptide or derivative thereof having at least one functional group protected by a protecting group, e.g. a lower alkyl ester of N-benzyloxycarbonyl-$\alpha$-L-aspartyl-L-phenylalanine by catalytic hydrogen reduction to produce free amino acid, peptide or derivative thereof. In contrast to the conventional procedures in which the reaction is carried out in a solvent dissolving both the starting compound and the product compound or a solvent dissolving the starting compound but not dissolving the product compound, the inventive method utilizes a binary two-phase reaction medium composed of water and an organic solvent not freely miscible with water such as toluene. The reaction takes place in the organic phase containing the starting compound dissolved and the catalyst dispersed therein whereas the reaction product which is water-soluble is smoothly and successively transferred into the aqueous phase so that advantages are obtained in the unexpectedly high yield of the product as well as in the easiness of handling the reaction mixture after completion of the reaction.

3 Claims, No Drawings

METHOD FOR REDUCTIVE ELIMINATION OF PROTECTING GROUPS

BACKGROUND OF THE INVENTION

The present invention relates to a method for reductive elimination of a protecting group from an amino acid or a peptide as well as a derivative thereof such as esters or amides having at least one functional group protected by the protecting group.

It is well known in the art that, in the course of synthetic preparation of many kinds of amino acids or peptides, the final stage of the process may be the reductive elimination of a protecting group from a protected amino acid or peptide having at least one functional group protected by the protecting group so as that the protected amino acid or peptide is converted into the desired product. It is usual in the prior art that the reaction of the above reductive elimination of the protecting proups is carried out in a solution with an organic solvent capable of dissolving both the protected starting material and the freed amino acid, peptide or derivative thereof in the presence of a catalyst for hydrogen reduction as dipersed therein. A problem in this procedure is that, owing to the solubility behavior of the starting material and the product in the solvent, it is sometimes difficult to obtain clear separation of the product from the unreacted starting material or from the catalyst.

On the other hand, it has been proposed to use such a solvent as the reaction medium that the starting material can be dissolved but the product compound is hardly soluble therein. In this case, the reaction mixture exhibits a slurry-like or gel-like consistency at a stage where the desired reaction has proceeded to some extent and the completeness of the reaction cannot be expected presenting a great practical drawback even by setting aside the disadvantage of troublesome handling of such a slurry-like or gel-like reaction mixture of high consistency.

The above situation is specifically explained for the preparation of a lower alkyl, e.g. methyl, ester of α-L-aspartyl-L-phenylalanine as a typical example. The above compound is a promising artificial sweetening agent and it has been eagerly desired to develop an efficient and economical method for the synthetic preparation thereof. The synthetic preparation of the compound is most conveniently performed by the route of an N-benzyloxycarbonyl-substituted compound as an intermediate and the final stage of the process is the elimination of the benzyloxycarbonyl group from the substituted intermediate compound by the catalytic reduction with hydrogen to liberate the desired compound. This reductive elimination reaction of the benzyloxycarbonyl group is usually carried out in a mixed solvent of water and methyl alcohol but one of the problems involved in this process is, in addition to the above described disadvangates in the reductive elimination of the protecting groups in general, that a diketopiperazine is unavoidably produced leading to a great decrease in the yield of the desired compound.

SUMMARY OF THE INVENTION

It is therefore an object of the present invention to provide a novel and improved method for practicing the reaction of the reductive elimination of a protecting group from an amino acid, peptide or derivative thereof having at least one functional group protected by the protecting group free from the above described disadvantages or problems, in which the reaction can proceed smoothly and rapidly to completion without presenting difficulties in handling the reaction mixture following the reaction.

Another object of the present invention is to provide a novel and improved method for the elimination of benzyloxycarbonyl group by the catalytic reduction with hydrogen from a lower alkyl, e.g. methyl, ester of N-benzyloxycarbonyl-α-L-aspartyl-L-phenylalanine in which, in addition to the above mentioned general advantages, the undesirable diketopiperazine formation is greatly decreased.

Thus, the inventive method for the reductive elimination of a protecting group from an amino acid or peptide as well as a derivative thereof having at least one functional group protected by the protecting group comprises subjecting the amino acid, peptide or derivative thereof to catalytic reduction in a binary reaction medium composed of water and an organic solvent not freely miscible with water forming two separate liquid phases to reductively eliminate the protecting group from the amino acid, peptide or derivative thereof.

In particular, the above described inventive method is most successfully applicable to the reductive elimination of benzyloxycarbonyl group from a lower alkyl, e.g. methyl, ester of N-benzyloxycarbonyl-α-L-aspartyl-L-phenylalanine by the catalytic reduction with hydrogen, in which the most preferred organic solvent not freely miscible with water is toluene.

DETAILED DESCRIPTION OF THE PREFERRED EMBODIMENTS

In view of the above described problems in the reductive elimination of a protecting group from a protected amino acid, peptide or derivative thereof, the inventors have conducted extensive investigations to overcome the difficulties in the prior art and arrived at a discovery that the most effective way for overcoming the prior art difficulties is to carry out the reaction of the catalytic reduction in a binary reaction medium composed of water and an organic solvent not freely miscible with water forming two separate phases leading to the establishment of the present invention.

The starting material to which the inventive method is applicable is a protected amino acid, peptide or derivative thereof having at least one of amino groups and carboxyl groups, optionally, together with one or more of hydroxyl groups in a molecule as the functional groups, at least one of these functional groups being protected by the substitution of a protecting group such as a nucleus-substituted or unsubstituted benzyl or benzyloxycarbonyl group or the like. Examples of the derivatives include a lower alkyl, e.g. of up to 3 carbon atoms, ester, benzyl ester and an amide such as glutamine or asparagine. Typical examples of these protected amino acids, peptides and derivatives thereof are:

N-benzyloxycarbonyl-alanine;
N-benzyl-leucine;
benzyl ester of leucine;
N-benzyloxycarbonyl-O-benzyl-serine;
N-benzyloxycarbonyl-leucyl-glycine;
N-benzyl-leucyl-glycine;
methyl ester of N-benzyl-α-L-aspartyl-L-phenylalanine;
N-benzyloxycarbonyl-O-benzyl-seryl-leucine;
N-benzyloxycarbonyl-L-leucyl-L-phenylalanine;
N-benzyloxycarbonyl-DL-aspartic acid;

benzyl ester of L-phenylalanine;
β-benzyl ester of L-aspartic acid;
benzyl ester of N-benzyloxycarbonyl-leucyl-glycine;
γ-ethyl ester of N-benzyloxycarbonyl glutamic acid;
lower alkyl esters of N-benzyloxycarbonyl-α- or β-L-aspartyl-L-phenylalanine;
methyl ester of O-benzylserine; and
β-benzyl ester of N-benzyloxycarbonyl aspartic acid.

It is of course that the starting compound used in the inventive method may have two or more of the functional groups each protected by a protecting group.

The reaction medium in the reaction of the inventive method is a binary mixture of water and an organic solvent not freely miscible with water forming two separate phases. Suitable organic solvents include aromatic hydrocarbons such as benzene, toluene and xylene, halogenated hydrocarbon solvents such as 1,2-dichloroethane and methylene chloride and ester solvents such as ethyl acetate and butyl acetate. The organic solvent forms a separate phase from the aqueous phase. In other words, the water and the organic solvent must be used in such amounts not to form a unifrom single phase by the mutual dissolution but to form two separate phases. The reaction medium may contain a small amount of an organic solvent miscible with water such as an alcohol or acetic acid, if desired.

Total volume of the reaction medium is desirably so large that smooth agitation of the reaction mixture containing the reactant and the catalyst is ensured. The amount of the organic solvent should desirably be sufficient to dissolve all of the starting reactant compound but the reaction can be performed with so small an amount of the organic solvent that a suspension or slurry of the starting reactant is formed provided that the consistency of the suspension or slurry is not excessively high to prevent smooth agitation of the reaction mixture. It is natural that the use of an excessive amount of the organic solvent is undesirable by the reason of the decreased efficiency in the treatment of the reaction mixture after completion of the reaction. On the other hand, water is desirably used in an amount sufficient to dissolve all of the product formed by the reductive elimination of the protecting group from the starting protected compound. It is also natural that the use of an excessive amount of water is undesirable because of the decreased efficiency in the separation of the product from the aqueous reaction medium.

Except for the above described conditions of the reaction medium, the other conditions for the elimination reaction of the protecting groups by the catalytic reduction with hydrogen are rather conventional. The catalyst used in the reaction can be a conventional palladium or nickel catalyst and the amount of the catalyst, reaction temperature, the manner for blowing hydrogen gas into the reaction mixture and the like conditions are determined according to ordinarily practiced procedures.

In practicing the method of the present invention, the starting compound having the protecting groups is first dissolved in the phase of the organic solvent which also contains the catalyst as suspended therein. As the reaction proceeds, the product compound formed in the organic phase by the elimination of the protecting groups is transferred into the aqueous phase successively. After completion of the reaction, the catalyst is removed, e.g. by filtering, from the reaction mixture and the remainder is subjected to liquid-liquid phase separation into the organic solution containing solvent-soluble materials to be recovered and the aqueous solution containing the product compound as separated from the unreacted starting compound. The catalyst may be removed after the liquid-liquid phase separation. It is an easy matter to isolate the desired amino acid, peptide or derivative thereof from the aqueous solution according to need by a conventional procedure such as crystallization and the like.

In particular, the method of the present invention is most successfully applicable to the preparation of a lower alkyl ester of α-L-aspartyl-L-phenylalanine by the elimination of N-benzyloxycarbonyl group from the corresponding lower alkyl ester of N-benzyloxycarbonyl-α-L-aspartyl-L-phenylalanine by using toluene as the water-immiscible organic solvent. Further detailed description is given below for this particular case.

In the prior art processes for the elimination of the benzyloxycarbonyl group from a lower alkyl ester of N-benzyloxycarbonyl-α-L-aspartyl-L-phenylalanine by the catalytic reduction with hydrogen, a problem is the formation of the diketopiperazine as is mentioned above leading to unavoidable decrease in the yield of the desired compound to a great extent. In the method of the present invention, on the contrary, the undesirable diketopiperazine formation is so small as to be negligible practically. The elimination of the benzyloxycarbonyl groups proceeds efficiently and smoothly in the two-phase reaction medium composed of water and toluene chosen as one of the most effective organic solvents and further the by-product formed by the elimination of the benzyloxycarbonyl groups is toluene which is the same compound as the organic solvent used as the reaction medium so that no problems are involved in the separation of the by-product greatly facilitating treatment of the reaction mixture after reaction.

The lower alkyl esters of N-benzyloxycarbonyl-α-L-aspartyl-L-phenylalanine as the starting compound in this particular process according to the invention can be obtained either synthetically by the reaction of a lower alkyl ester of L-phenylalanine and anhydride of N-benzyloxycarbonyl-L-aspartic acid or by the enzymatic reaction between a lower alkyl ester of L-phenylalanine and N-benzyloxycarbonyl-L-aspartic acid. In the former method, the reaction mixture after the reaction can be used as such as the starting material of the inventive process while, in the latter enzymatic method, the addition compound of the lower alkyl ester of phenylalanine and the lower alkyl ester of N-benzyloxycarbonyl-α-L-aspartyl-L-phenylalanine as the product of the enzymatic reaction is decomposed with an acid followed by extraction with an organic solvent to give an extract which can be used as the starting material of the inventive process. In any case, the above obtained starting solution may be concentrated by evaporation or other means according to need before use. Crude cryltals obtained by crystallization from the reaction mixture can also be used. In the prior art, such crude crystals are dissolved in an alcohol or a hydrated alcohol whereas, in the method of the present invention, the crude crystals separated from the reaction mixture are subjected to the elimination reaction in a two-phase reaction medium. Accordingly, the reaction mixture as such or a concentrate thereof can be used in the method of the invention to fully exhibit the expected effects of the invention even when the starting solution contains an alcohol provided that the amount of the alcohol is not excessively large.

The volume of water used as one of the components of the two-phase reaction medium is preferably in the range from about 5 to about 30 liters per mole of the lower alkyl ester of N-benzyloxycarbonyl-α-L-aspartyl-L-phenylalanine. The volume of toluene as the other component of the reaction medium is preferably limited to a volume as small as possible in so far as the starting compound having protecting groups can be dissolved therein or, at least, sufficient fluidity can be obtained in the slurry of the starting compound in the solvent. The volume is usually in the range from about 2 to 70 liters of toluene per mole of the lower alkyl ester of N-benzyloxycarbonyl-α-L-aspartyl-L-phenylalanine.

The lower alkyl ester of N-benzyloxycarbonyl-α-L-aspartyl-L-phenylalanine as the starting compound is dissolved in toluene and, as the reaction of elimination proceeds, the lower alkyl ester of α-L-aspartyl-L-phenylalanine as the product formed in the organic phase is transferred into the aqueous phase.

After completion of the reaction and after or before removal of the catalyst, e.g. by filtration, the reaction mixture is subjected to liquid-liquid phase separation into the organic solution containing the unreacted starting compound, if any, and the aqueous solution. Toluene-soluble materials such as the unreacted starting compound can be recovered from the thus separated organic solution while the aqueous solution contains the desired product in a purified form by the elimination of the benzyloxycarbonyl groups.

As is described above, the method of the present invention utilizes a two-phase reaction medium composed of water and a water-immiscible organic solvent such as toluene and the starting compound is dissolved or at least partly dissolved to form a suspension in the organic phase while the reaction product is dissolved in the aqueous phase. Thus, the reaction of the elimination takes place solely in the organic phase and the reaction product formed therein is successively transferred into the aqueous phase. As a result, the reaction mixture after completion of the reaction is composed of the organic phase containing the unreacted starting compound, if any, and the aqueous phase containing the reaction product so that the separation of the product compound from the unreacted starting compound is very easily performed by the simple liquid-liquid phase separation of both phases. Further, the catalyst used in the reaction is suspended in the organic phase so that there is no problem of separating it from the reaction product. An additional advantage of the inventive method is the very small yield of by-products to give, as a consequence, a very high yield of the desired compound from which the protecting groups have been eliminated.

In the following, the inventive method is described in further detail by way of examples.

EXAMPLE 1

In a four-necked flask was dissolved or suspended 9.9 g of methyl ester of N-benzyloxycarbonyl-α-L-aspartyl-L-phenylalanine into a binary reaction medium composed of water and toluene or methyl alcohol in amounts as indicated in Table 1 below. After complete replacement of the air in the flask with nitrogen gas, 0.2 g of a palladium catalyst containing 5% by weight of palladium supported on carbon carrier was introduced into the reaction mixture and the hydrogen reduction was carried out by blowing hydrogen gas into the reaction mixture with agitation for 5 hours while the temperature of the mixture was kept at 50° C. After completion of the reaction, the catalyst was removed by filtration and the filtrate was kept standing for a short while to be separated into the layer of toluene initially added or formed by the reaction and the aqueous layer containing the reaction products in water or in a mixture of water and methyl alcohol. The aqueous solution was analyzed by thin-layer chromatography to determine the yields of the desired compound and by-products. The results are set out in Table 1 below, in which the symbols APM, DKP and AP denote methyl ester of β-L-aspartyl-L-phenylalanine, diketopiperazine of α-L-aspartyl-L-phenylalanine and β-L-aspartyl-L-phenylalanine, respectively, and the values of the yields are all given on the base of the starting methyl ester of N-benzyloxycarbonyl-α-L-asparyl-L-phenylalanine.

TABLE 1

| Experiment No. | | Present invention | | Control | |
|---|---|---|---|---|---|
| | | 1 | 2 | 3 | 4 |
| Reaction mixture, ml | Water | 250 | 130 | 250 | 250 |
| | Toluene | 500 | 160 | — | — |
| | Methyl alcohol | — | — | 500 | 250 |
| Yield of product, % | APM | 99.3 | 99.5 | 90.2 | 92.7 |
| | DKP | 0.5 | 0.3 | 9.4 | 6.8 |
| | AP | 0.2 | 0.2 | 0.4 | 0.5 |

EXAMPLE 2

A reaction mixture was prepared by dissolving a mixture of 8.6 g of methyl ester of N-benzyloxycarbonyl-α-L-aspartyl-L-phenylalanine and 2.1 g of methyl ester of N-benzyloxycarbonyl-β-L-aspartyl-L-phenylalanine in a binary reaction medium composed of 500 ml of toluene and 250 ml of water followed by complete replacement of the air in the flask with nitrogen gas and addition of 0.2 g of the same palladium catalyst as used in Example 1. The reaction of reduction was conducted by blowing hydrogen gas into the reaction mixture at 60° C. for 5 hours with agitation. After completion of the reaction, the catalyst was removed by filtration from the reaction mixture and the filtrate was kept standing to be separated into the upper toluene layer and the lower aqueous layer. After the toluene solution was removed by liquid-liquid phase separation, the aqueous solution was analyzed by thin-layer chromatography to find that the aqueous solution contained 5.86 g of methyl ester of α-L-aspartyl-L-phenylalanine corresponding to a 99.5% yield based on the starting methyl ester of N-benzyloxycarbonyl-α-L-aspartyl-L-phenylalanine, 0.02 g of diketopiperazine corresponding to a 0.4% yield based on the same starting compound and 1.44 g of methyl ester of β-L-aspartyl-L-phenylalanine corresponding to a 99.9% yield based on the starting methyl ester of N-benzyloxycarbonyl-β-L-aspartyl-L-phenylalanine.

EXAMPLE 3

A reaction mixture was prepared by dissolving 2.0 g of methyl ester of N-benzyloxycarbonyl-α-L-aspartyl-L-phenylalanine in a binary reaction medium composed of 90 g of ethyl acetate and 100 g of water followed by complete replacement of the air in the flask with nitrogen gas and addition of 0.12 g of the same palladium catalyst as used in Example 1. The reaction of reduction was carried out by blowing hydrogen gas into the reaction mixture at 60° C. for 3 hours with agitation. After completion of the reaction, the catalyst was removed by filtration and the filtrate was kept standing to be separated into the upper organic layer and the lower aqueous later. The aqueous solution thus obtained was analyzed by high-speed liquid chromatography to find that the solution contained 1.35 g of methyl ester of α-L-aspartyl-L-phenylalanine, 0.009 g of diketopiperazine and 0.004 g of α-L-aspartyl-L-phenylalanine corresponding to yields of 98.5%, 0.7% and 0.3%, respectively, all based on the starting methyl ester of N-benzyloxycarbonyl-α-L-aspartyl-L-phenylalanine.

The analytical conditions for the high-speed liquid chromatography were as follows.

(a) Columns: a column of 7.5 mm inner diameter and 20 cm length filled with starch gel having an average particle diameter of about 5 μm (TSK GEL LS-170, a product by Toyo Soda Kogyo Co.) was used for the analysis of methyl ester of α-L-aspartyl-L-phenylalanine and a column of 4.0 mm inner diameter and 10 cm length filled with a cation exchange resin having an average particle diamter of about 5 μm (TSK GEL IEX-210, a product by the same company) and a column of 7.5 mm inner diameter and 40 cm length filled with the starch gel TSK GEL LS-170 were used for the analysis of α-L-aspartyl-L-phenylalanine and diketopiperazine.

(b) Eluant solution: 0.8% by weight aqueous solution of sodium acetate (c) Flow rate: 0.91 ml/minute (d) Temperature: 25° C.

(e) Detector: ultraviolet detector (Model UVIDEC-II, manufactured by Nippon Bunko Co.)

(f) Wavelength of the ultraviolet light: 256 nm

EXAMPLE 4

A reaction mixture was prepared by dissolving 4.0 g of methyl ester of N-benzyloxycarbonyl-α-L-aspartyl-L-phenylalanine in a binary reaction medium composed of 120 g of 1,2-dichloroethane and 100 g of water followed by replacement of the air in the flask with nitrogen gas and addition of 0.80 g of the same palladium catalyst as used in Example 1. The reaction of reduction was carried out by blowing hydrogen gas into the reaction mixture at 60° C. for 3 hours with agitation. The treatment of the reaction mixture after completion of the reaction was carried out in the same manner as in Example 3 and the aqueous solution was analyzed to find that the aqueous solution contained 2.72 g of methyl ester of α-L-aspartyl-L-phenylalanine and 0.012 g of diketopiperazine corresponding to yields of 99.1% and 0.5%, respectively, both based on the starting methyl ester of N-benzyloxycarbonyl-α-L-aspartyl-L-phenylalanine with only a trace amount of α-L-aspartyl-L-phenylalanine.

EXAMPLE 5

A reaction mixture was prepared by suspending 0.20 g of methyl ester of N-benzyl-α-L-aspartyl-L-phenylalanine in a binary reaction medium composed of 50 g of benzene and 50 g of water followed by replacement of the air in the flask with nitrogen gas and addition of 0.1 g of the same palladium catalyst as used in Example 1. The reaction of reduction was conducted by blowing hydrogen gas into the reaction mixture at 60° C. for 5 hours with agitation. The reaciton mixture after completion of the reaction was treated and analyzed in the same manner as in Example 3 to find that the yield of methyl ester of α-L-aspartyl-L-phenylalanine was 0.133 g corresponding to a yield of 97.0% based on the starting N-benzyl-α-L-aspartyl-L-phenylalanine methyl ester.

EXAMPLE 6

A reaction mixture was prepared by dissolving 0.21 g of N-benzyloxycarbonyl-L-leucyl-L-phenylalanine in a binary reaction medium composed of 50 g of toluene and 50 g of water followed by replacement of the air in the flask with nitrogen gas and addition of 0.1 g of the same palladium catalyst as used in Example 1. The reaction of reduction was conducted by blowing hydrogen gas into the reaction mixture at 60° C. for 3 hours with agitation. After completion of the reaction, the catalyst was removed by filtration from the reaction mixture and the aqueous solution after liquid-liquid phase separation of the filtrate was evaporated to dryness to leave 0.14 g of dry crystals of L-leucyl-L-phenylalanine having a melting point of 216° to 218° C. and $[\alpha]_D^{25}$ of +7.30 (c=1 in 2.5 NHCl). The yield was almost 100% of the theoretical value.

EXAMPLE 7

A reaction mixture was prepared by dissolving 5.0 g of N-benzyloxycarbonyl-DL-aspartic acid in a binary reaction medium composed of 90 g of ethyl acetate and 150 g of water followed by replacement of the air in the flask with nitrogen gas and addition of 0.3 g of the same palladium catalyst as used in Example 1. The reaction was carried out in the same manner as in Example 3 for 3 hours and the aqueous solution after completion of the reaction and phase separation contained 2.46 g of DL-aspartic acid as analyzed by high-speed liquid chromatography corresponding to 98.9% of the theoretical yield.

EXAMPLE 8

A reaction mixture was prepared by dissolving 4.27 g of benzyl ester of L-phenylalanine in the form of a p-toluenesulfonate in a binary reaction medium composed of 90 g of ethyl acetate and 100 g of a 0.4% aqueous solution of sodium hydroxide followed by replacement of the air in the flask with nitrogen gas and addition of 0.3 g of the same palladium catalyst as used in Example 1. The reaction of reduction was conducted by blowing hydrogen gas into the reaction mixture at 70° C. for 3 hours with agitation. After completion of the reaction, the reaction mixture was treated and analyzed in the same manner as in Example 3 to find that the aqueous phase contained 1.39 g of L-phenylalanine corresponding to 84% of the theoretical yield.

EXAMPLE 9

A reaction mixture was prepared by dissolving 3.0 g of β-benzyl ester of L-aspartic acid in a binary reaction medium composed of 100 g of ethyl acetate and 100 g of water followed by replacement of the air in the flask with nitrogen gas and addition of 0.3 g of the same palladium catalyst as used in Example 1. The reaction of reduction was conducted by blowing hydrogen gas into the reaction mixture at 60° C. for 4 hours with agitation. After completion of the reaction, the reaction mixture was treated and analyzed in the same manner as in Example 3 to find that the aqueous phase contained 1.48 g of L-aspartic acid corresponding to 84.6% of the theoretical yield.

After liquid-liquid phase separation, the organic solution was evaporated to dryness under reduced pressure and the aqueous solution obtained by dissolving the residue in water was analyzed by high-speed liquid chromatography in the same manner as in Example 3 to detect the presence of the starting β-benzyl ester of L-aspartic acid. On the other hand, no starting compound was detected in the aqueous solution obtained by the liquid-liquid phase separation.

What is claimed is:

1. In a method for eliminating a benzyloxycarbonyl group from a lower alkyl ester of N-benzyloxycarbonyl-α-L-aspartyl-L-phenylalanine by catalytic reduction with hydrogen in a liquid reaction medium, an improvement which comprises using a two-phase medium composed of water and toluene as the liquid reaction medium.

2. The improvement as claimed in claim 1 wherein the volumes of water and toluene are from about 5 to about 30 liters and from about 2 to about 70 liters, respectively, per mole of the lower alkyl ester of N-benzyloxycarbonyl-α-L-aspartyl-L-phenylalanine.

3. A method for the preparation of a lower alkyl ester of α-L-aspartyl-L-phenylalanine from a corresponding lower alkyl ester of N-benzyloxycarbonyl-α-L-aspartyl-L-phenylalanine which comprises the steps of
(a) dispersing said lower alkyl ester of N-benzyloxycarbonyl-α-L-aspartyl-L-phenylalanine in a two-phase binary liquid reaction medium composed of water and toluene to form a reaction mixture,
(b) blowing hydrogen into the reaction mixture in the presence of a catalyst whereby the benzyloxycarbonyl group is eliminated, and
(c) subjecting the reaction mixture to liquid-liquid phase separation into the toluene and an aqueous solution containing the lower alkyl ester of α-L-aspartyl-L-phenylalanine.

* * * * *